(12) United States Patent
Huang

(10) Patent No.: US 11,054,422 B2
(45) Date of Patent: Jul. 6, 2021

(54) CIRCULATING ASTROCYTES AND MFSD2A AS BIOMARKERS

(71) Applicants: Sheng-He Huang, Arcadia, CA (US); Alec Chan, San Gabriel, CA (US)

(72) Inventor: Sheng-He Huang, Arcadia, CA (US)

(73) Assignees: Sheng-He Huang, Arcadia, CA (US); Alec Chan, San Gabriel, CA (US)

( * ) Notice: Subject to any disclaimer, the term of this patent is extended or adjusted under 35 U.S.C. 154(b) by 0 days.

(21) Appl. No.: 16/431,559

(22) Filed: Jun. 4, 2019

(65) Prior Publication Data

US 2019/0293647 A1 Sep. 26, 2019

Related U.S. Application Data

(62) Division of application No. 15/436,859, filed on Feb. 19, 2017, now Pat. No. 10,345,302.

(51) Int. Cl.
*G01N 33/569* (2006.01)
*A61K 45/00* (2006.01)
*A61K 31/13* (2006.01)

(52) U.S. Cl.
CPC ....... *G01N 33/56966* (2013.01); *A61K 45/00* (2013.01); *A61K 31/13* (2013.01); *G01N 2333/70571* (2013.01); *G01N 2800/2871* (2013.01); *G01N 2800/50* (2013.01)

(58) Field of Classification Search
CPC ..... G01N 33/56966; G01N 2800/2871; G01N 2333/70571; G01N 2800/50; G01N 33/6896; G01N 2800/52
See application file for complete search history.

*Primary Examiner* — Olga N Chernyshev
(74) *Attorney, Agent, or Firm* — ScienBiziP, P.C.

(57) ABSTRACT

The invention provides the use of circulating astrocytes (cAstr) and the Major Facilitator Superfamily Domain containing Protein 2a (Mfsd2a) as biomarkers, and their combined use with other related circulating markers (cBMEC and EPC) in early detection and diagnosis of cerebrovascular diseases (CVD) or central nervous system (CNS) disorders.

3 Claims, 6 Drawing Sheets

CIRCULATING ASTROCYTES AND MFSD2A AS BIOMARKERS

This is a divisional of application Ser. No. 15/436,859, filed Feb. 19, 2017; the contents of the above-named application are fully incorporated herein by reference for all purposes.

STATEMENT REGARDING FEDERALLY-SPONSORED RESEARCH

The invention was made with government support under Grant Nos. AI040635, NS083967 and DA034515 awarded by the National Institutes of Health, and 81370740 by National Science Foundation (NSF)-CN. The governments have certain rights to the invention.

FIELD

The invention relates to processes, assays and methods for detecting cerebrovascular diseases (CVD) or central nervous system (CNS) disorders, and method for treating the same.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

CVD and CNS disorders caused by microbial infection, external mechanical force to the brain (e.g. traumatic brain injury), stroke, drug abuse, brain tumor, or neurodegenerative diseases, remain to be the world's leading causes of death and disabilities despite aggressive researches. The brain is the most delicate organ of the body. It is protected by the blood-brain barrier (BBB). Diseases associated with neurovascular unit (NVU) or BBB injuries account for more hospitalizations and prolonged care than almost all other diseases combined. Patients experiencing devastating CVD or CNS diseases far outnumber those suffering and dying from all types of systemic cancers or heart diseases. Over one-third of the entire population will experience a CNS disorder during their lifetime. CVD is most commonly associated with high blood pressure (HBP, hypertension). About one in three American adults (32%) has HBP, whereas another 1 in 3 American adults has prehypertension. The incidence of CVD and CNS disorders increases with age.

NeuroAIDS as a form of microbial infection of the brain is a significant cause of CNS disorder. The prevalence of NeuroAIDS has increased recently despite advances in highly active antiretroviral therapy. This is mainly due to the inability of antiretroviral drugs to cross the BBB and the role of CNS as the reservoir for HIV-1, a virus that is capable of freely migrating in and out of the brain. The incidence of NeuroAIDS is higher or accelerated among the aging populations and drug users.

Quantitative evaluation of NVU or BBB damages has been one of the most challenging issues in researching CVD or CNS disorders caused by microbial and non-microbial insults. Successful isolation and cultivation of brain microvascular endothelial cells (BMECs), which are the relevant in vitro model of the NVU or BBB, has enabled both molecular characterization and genome-wide analysis of the pathogenic mechanisms of BBB injuries attributable to microbial or non-microbial factors in vitro. However, it is difficult to carry out genome-wide, noninvasive evaluation of NVU or BBB injuries in vivo.

A variety of methods have been used to evaluate the function of the NVU or BBB in vivo. Leakage of peripheral proteins such as fibrinogen and albumin into the CNS has been used to evaluate BBB permeability associated with viral encephalitis and other CNS infection. While these techniques have the advantage of using endogenous proteins, the NVU or BBB injury may not correlate well with the protein levels in CNS due to certain nonspecific effects. Recent studies show that there are no blood tests utilizing a molecular biomarker that can accurately determine the presence or the severity of cerebrovascular disorders (CVD) such as traumatic brain injury (TBI) because no clinical tools are available for measuring glymphatic-derived convective bulk flow of the molecular movements within the brain's interstitium.

Recently, magnetic resonance (MRI)-based molecular imaging technologies have gained increasing attention in neuroscience. Although an increasing number of synthesized molecular imaging agents have been tested in vitro, very few have been validated in the brains of live animals. The major challenges in molecular neuroimaging approaches are the poor ability of delivering agents across the BBB. Other methods involve the injection of dyes, such as Evans blue and sodium fluorescein, into a variety of animal model systems for evaluation of BBB permeability. The main limitation of these techniques is that they cannot be used in humans.

Despite the identification of hundreds of molecular markers by preclinical and clinical researches over the past few decades, there is currently no blood test clinically available for objective evaluation of the presence or severity of NVU or BBB injuries. Therefore, there exists a need for noninvasive biomarkers to address the problem of the diagnosis, prognosis, prevention, and treatment of the CVD or CNS disorders.

SUMMARY

The following embodiments and aspects thereof are described and illustrated in conjunction with systems, compositions and methods which are meant to be exemplary and illustrative, not limiting in scope.

Provided herein is a process that includes the steps of obtaining a peripheral blood sample from a subject desiring to know the likelihood of carrying central nervous system or neurovascular unit disorder, of assaying the sample to determine the density of circulating astrocytes (cAstr) as well as circulating brain microvascular endothelial cells (cBMEC) to determine that the subject has an increased likelihood of CNS or NVU disorder, depending on whether the subject has exhibited higher levels of cAstr or cBMEC relative to the reference sample. Further described herein are assays for diagnosing and selecting therapy for such subject having CNS or NVU disorder, and optionally administering the therapy.

Also provided herein is a process that includes the steps of obtaining a peripheral blood sample from a subject desiring to know the likelihood of carrying CNS or NVU disorder, assaying the sample to determine levels of MfSD2a, and determining the subject has an increased likelihood of CNS or NVU disorder if level of MfSD2a is increased relative to a reference sample, or determining the subject has decreased likelihood of CNS or NVU disorder if the levels of MfSD2a is the same as or decreased relative to the reference sample. Further described herein are assays for diagnosing and selecting therapy for such subject having CNS or NVU disorder, and optionally administering the therapy.

Also provided herein is a process that includes the steps of obtaining a sample from a subject desiring to know the likelihood of carrying CNS or NVU disorder, assaying the sample to determine levels of MfSD2a-containing cells, and determining the subject has an increased likelihood of CNS or NVU disorder if level of MfSD2a-containing cells is increased relative to a reference sample, or determining the subject has decreased likelihood of CNS or NVU disorder if the levels of MfSD2a-containing cells is the same as or decreased relative to the reference sample. Further described herein are assays for diagnosing and selecting therapy for such subject having CNS or NVU disorder, and optionally administering the therapy.

BRIEF DESCRIPTION OF THE DRAWINGS

Exemplary embodiments are illustrated in referenced figures. It is intended that the embodiments and figures disclosed herein are to be considered illustrative rather than restrictive.

DETAILED DESCRIPTIONS

Figure 1:
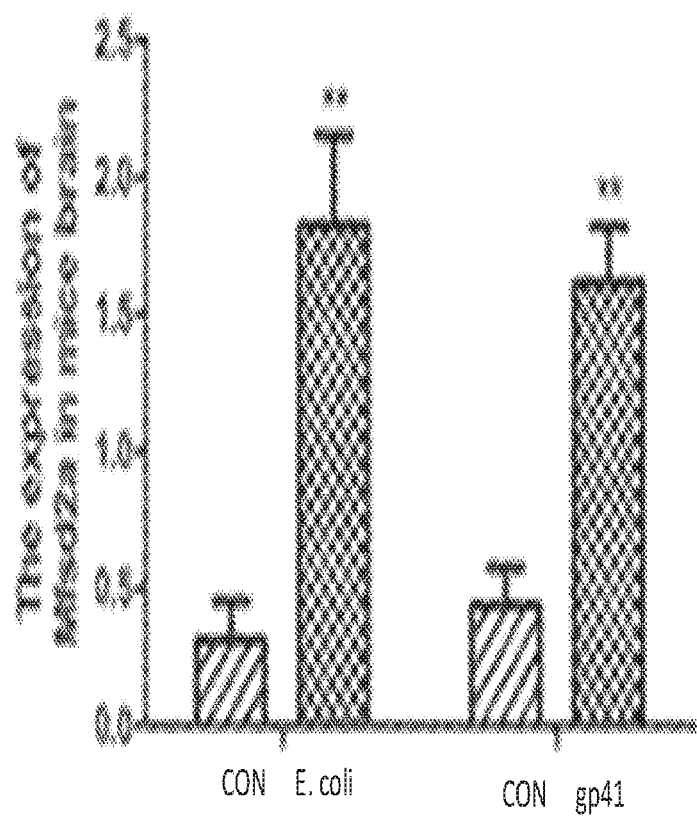
FIG. 1 demonstrates increased expression of Mfsd2a in the brains of mouse models. The mice were stimulated with *E. coli* K1, or HIV-1 virulence factor gp41. The level of Mfsd2a in the brain is quantitated by western blotting analysis. Western result shows increased level of Mfsd2a in the brain of *E. coli*-infected and gp41-treated mice. The level of Mfsd2a in mouse brain stimulated by *E. coli* is measured by Bio-Rad Gel Doc 2000 Systems with Bio-Rad TDS Quantity One software against the β-actins as controls. All data are represented as Means±SEM and expressed as the intensity/mm$^2$. *<0.05; **<0.01 vs. controls. CON, Control. n=4 liters (3 biological replicates).

Unless defined otherwise, technical and scientific terms used herein have the same meaning as commonly understood by one of ordinary skill in the art to which this invention belongs. The practice of the present invention will employ, unless indicated specifically to the contrary, conventional methods of molecular biology and recombinant DNA techniques within the skill of the art, many of which are described below for the purpose of illustration. Such techniques are fully explained in the literature. See, e.g., Singleton et al., Dictionary of Microbiology and Molecular Biology 3rd ed., J. Wiley & Sons (New York, N.Y. 2001); March, Advanced Organic Chemistry Reactions, Mechanisms and Structure 5th ed., J. Wiley & Sons (New York, N.Y. 2001), Sambrook, et al., Molecular Cloning: A Laboratory Manual (3rd Edition, 2000); Sambrook and Russel, Molecular Cloning: A Laboratory Manual 3rd ed., Cold Spring Harbor Laboratory Press (Cold Spring Harbor, N.Y. 2001), DNA Cloning: A Practical Approach, vol. I & II (D. Glover, ed.); Oligonucleotide Synthesis (N. Gait, ed., 1984); Oligonucleotide Synthesis: Methods and Applications (P. Herdewijn, ed., 2004); Nucleic Acid Hybridization (B. Hames & S. Higgins, eds., 1985); Nucleic Acid Hybridization: Modern Applications (Buzdin and Lukyanov, eds., 2009); Transcription and Translation (B. Hames & S. Higgins, eds., 1984); Animal Cell Culture (R. Freshney, ed., 1986); Freshney, R. I. (2005) Culture of Animal Cells, a Manual of Basic Technique, 5th Ed. Hoboken N.J., John Wiley & Sons; B. Perbal, A Practical Guide to Molecular Cloning (3rd Edition 2010); Farrell, R., RNA Methodologies: A Laboratory Guide for Isolation and Characterization (3rd Edition 2005), Methods of Enzymology: DNA Structure Part A: Synthesis and Physical Analysis of DNA Methods in Enzymology, Academic Press; Using Antibodies: A Laboratory Manual: Portable Protocol No. 1 by Edward Harlow, David Lane, Ed Harlow (1999, Cold Spring Harbor Laboratory Press, ISBN 0-87969-544-7); Antibodies: A Laboratory Manual by Ed Harlow (Editor), David Lane (Editor) (1988, Cold Spring Harbor Laboratory Press, ISBN 0-87969-3, 4-2), 1855. Handbook of Drug Screening, edited by Ramakrishna Seethala, Prabhavathi B. Femandes (2001, New York, N.Y., Marcel Dekker, ISBN 0-8247-0562-9); and Lab Ref: A Handbook of Recipes, Reagents, and Other Reference Tools for Use at the Bench, Edited Jane Roskams and Linda Rodgers, (2002, Cold Spring Harbor Laboratory, ISBN 0-87969-630-3) provide one skilled in the art with a general guide to many of the terms used in the present application.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

"Beneficial results" may include, but are in no way limited to, lessening or alleviating the severity of the disease condition, preventing the disease condition from worsening, curing the disease condition, preventing the disease condition from developing, lowering the chances of a patient developing the disease condition and prolonging a patient's life or life expectancy. In some embodiments, the disease condition is a CNS disorder. In some embodiments, the disease condition is neurovascular unit or blood-brain barrier damage.

"Subject" or "individual" or "animal" or "patient" or "mammal," is meant any subject, particularly a mammalian subject, for whom diagnosis, prognosis, or therapy is desired. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on. In certain embodiments, the mammal is a human subject. The term does not denote a particular age or sex. Thus, adult and newborn subjects, as well as fetuses, whether male or female, are intended to be included within the scope of this term.

"Treatment" and "treating," as used herein refer to both therapeutic treatment and prophylactic or preventative measures, wherein the object is to prevent or slow down (lessen) the targeted pathologic condition, prevent the pathologic condition, pursue or obtain beneficial results, or lower the chances of the individual developing the condition even if the treatment is ultimately unsuccessful. Those in need of treatment include those already with the condition as well as those prone to have the condition or those in whom the condition is to be prevented. Examples of treatment include, but are not limited to, active surveillance, observation, surgical intervention, chemotherapy, immunotherapy, radiation therapy (such as external beam radiation, stereotactic radiosurgery (gamma knife), and fractionated stereotactic radiotherapy (FSR)), focal therapy, systemic therapy, vaccine therapies, viral therapies, molecular targeted therapies, or a combination thereof.

"Patient outcome" refers to whether a patient survives or dies as a result of treatment. A more accurate prognosis for patients as provided in this invention increases the chances of patient survival.

Despite aggressive research, CVD or CNS disorders, including NVU or BBB injury caused by, for example, microbial infection, stroke, abused drugs, or other pathogenic insults, remain the world's leading cause of disabilities. We previously found that dysfunction of astrocytes and brain microvascular endothelial cells (BMECs), which are the major components of the BBB, could be caused by nicotine, meningitic pathogens and microbial factors, including HIV-1 virulence factors gp41 and gp120. One of the most challenging issues in this area is that there are no available cell-based biomarkers in the peripheral blood for CVD or CNS disorders caused by microbial and non-microbial insults. To identify such cellular biomarkers for NVU or BBB injuries, our studies have shown that mice treated with nicotine, METH and gp120 resulted in increased blood levels of CD146+(endothelial marker)/S100B+(brain marker), circulating Astrocytes (cAstr), circulating BMECs (cBMECs) and CD133+[progenitor cell (PC) marker]/CD146+ endothelial PCs (EPCs), along with enhanced Evans blue and albumin extravasation into the brain. Nicotine and gp120 were able to significantly increase the serum levels of ubiquitin C-terminal hydrolase 1 as well as S100B in mice, which are correlated with the changes in cAstr and/or cBMECs. Nicotine- and meningitic E. coli K1-induced enhancement of cAstr and cBMEC levels, leukocyte migration across the BBB and albumin extravasation into the brain were significantly reduced in alpha7 nAChR knockout mice, suggesting that this inflammatory regulator plays an important role in CNS Inflammation and BBB disorders caused by microbial and non-microbial factors. These results demonstrated that cAstr as well as cBMECs may be used as potential cell-based biomarkers for detection of NVU or BBB injuries.

Accordingly, the invention is based, at least in part, on these findings. The present invention addresses the need for indicators for detection of CVD or CNS disorders such as damage to the NVU/BBB and for guiding treatment options. Provided herein are processes, assays and methods for detecting CVD or CNS disorders, such as damage to NVU or BBB and method for treating the same.

In various embodiments, the CVD or CNS disordersare any one or more of blood-brain-barrier damage, traumatic brain injury (TBI), CNS infection, epilepsy, stroke, brain tumor, neurodegenerative disorders, or a combination thereof. In an embodiment, the CVD or CNS disorder are blood-brain barrier damages. In exemplary embodiments, the blood-brain barrier damage may be due to diseases such as meningitis, brain abscess, epilepsy, multiple sclerosis, neuromyelitisoptica, late-stage neurological trypanosomiasis, progressive multifocal leukoencephalopathy, de vivo disease and/or Alzheimer's diseases.

In various embodiments, the sample is any one or more of tissue, blood, plasma, cerebrospinal fluids (CSF) or a combination thereof. In one embodiment, the sample is the peripheral blood.

The invention also provides a system for determining the presence of cAstr in a sample wherein the sample is obtained from a subject suspected of having BBB damage. The system includes a sample analyzer configured to produce a signal when cAstr cells are present in a sample obtained from a subject suspected of having BBB damage and a computer sub-system programmed to calculate, based on the density of cAstr cells detected whether the signal is greater than or not greater than a reference value.

In some embodiments of the systems, the subject is human and is suspected to have BBB damage. In some embodiments, the isolated sample is cells obtained through affinity purifying a blood sample with UEA-1-coated beads. In some embodiments, the detection module is a fluorescence microscope. In other embodiments of the system, the isolated sample is a blood sample. In other embodiments, the detection module is a flow cytometer or a fluorescence microscope. In various embodiments, the sample obtained from the subject is stained with at least one of an anti-CD146 antibody and an anti-MfSD2a antibody. The cBMEC cells may be identified by CD146+MfSD2a+ phenotype. In some embodiments, the sample is stained with at least one of an anti-CD45 antibody, an anti-CD31 antibody, and an anti-GLUT1 antibody and cBMEC cells are identified by GLUT1+CD31+CD45− phenotype. In various embodiments, the reference quantity of cBMEC cells is the mean or media quantity of cBMEC cells in a population of subjects without BBB damage.

Recently, quantification of circulating endothelial cells (CECs) in peripheral blood has been developed as a novel and reproducible approach for assessing endothelial damage or dysfunction caused by cardiovascular disorders and inflammatory diseases. The first descriptions of methods used to detect circulating cells in the blood with endothelial characteristics were reported in the mid-1970s. These methods included density centrifugation, vital light microscopy and histologic staining, which did not isolate and identify CECs reliably. It was two more decades before reliable procedures were developed to detect this rare cell population. Currently, the most common CEC quantification procedures include an enrichment step through immunomagnetic separation of cells using magnetic beads coupled to an antibody against an endothelial antigen such as CD146 (endothelial marker) or CD34 (progenitor cell marker). Among endothelial cells circulating in the blood, some are terminally differentiated mature cells (CECs) while others are showing progenitor-like phenotype [endothelial progenitor cells (EPCs)], suggesting that EPCs may participate in the generation of new vessels through homing to sites of angiogenesis. Over the past decade, increased CECs have been detected in many pathological conditions, including cancer and heart diseases. Such cell-based biomarkers, however, are not specifically identified in BBB disorders caused by CNS infection and inflammation. Since the BBB is mainly consisting of the specific set of endothelial cells called BMECs and astrocytes, it seems plausible that circulating BMECs (cBMECs) and astrocytes (cAstr) could be biomarkers for NVU or BBB injuries.

Based on our longstanding interest and studies in the NVU or BBB injuries and CVD or CNS disorders, we have hypothesized that cAstr and cBMECs, which are endowed with a full-blown NVU/BBB phenotype, are dynamically shedding from the NVU upon pathophysiological changes in the CNS. cAstr and BMECs can be monitored by experimental approaches and used as noninvasive blood biomarkers in indexing NVU or BBB injury, which is caused by various pathogenic insults. In our studies using animal model systems, we have demonstrated for the first time that NVU/BBB injury in mice could be detected by the technologies for characterization and quantification of cAstr and cBMECs derived from the CNS disorders caused by microbial (gp120 and E. coli K1) and non-microbial (methamphetamine) insults. Furthermore, we have also demonstrated that memantine (MEM), an alpha7 nAChR antagonist, could reduce the blood levels of cAstr and cBMEC, suggesting that this essential regulator of inflammation plays an important role in cAstr and cBMEC shedding associated with NVU and BBB injury caused by various pathogenic insults.

The major facilitator superfamily domain containing 2a (Mfsd2a) is a member of the major facilitator superfamily (MFS) of secondary-active transporter proteins. Previous work has shown that Mfsd2a expression is induced by factors in the liver during fasting, and the protein has also been implicated in antibiotic transport and in cell fusion in the human placenta. In a recent report, Mfsd2a was found to be selectively expressed in the BBB endothelium and required for normal formation and maintenance of the BBB integrity. Another research found that Mfsd2a is the major transporter mediating brain uptake of docosahexaenoic acid, an omega-3 fatty acid essential for normal brain growth and cognitive function. Moreover, Mfsd2a also serves as a cell-surface molecule to regulate membrane fusion or trafficking. These results suggest that Mfsd2a plays an important role in BBB functions.

In both in vitro and in vivo model systems, we have demonstrated that CVD and CNS disorders caused by microbial factors (E. coli and HIV) could induce change in the level of Mfsd2a in the brain. Furthermore, the BBB injury caused by E. coli K1 and HIV-1 virulence factor gp41 could increase the number of cBMEC captured with Mfsd2a biomarker in the peripheral blood.

Assays for Detecting cAstr

In various embodiments of the processes, assays, systems and methods described herein, determining the density of cAstr comprises quantitating the number of cells present in a sample obtained from the subject or the reference sample using manual or automated methods. In some embodiments, assay for quantitating the density of cAstr in the sample include but are not limited to any one or more of magnetic bead extraction (MBE), flow cytometry, measuring electrical resistance, staining, image analysis, assay using a hemocytometer, assay using a hemocytometer equipped with Neubauer grids, spectrophotometry, single cell technologies including microfluidics-based cell manipulation or a combination thereof [Zhong J F et. al. (2008), A microfluidic processor for gene expression profiling of single human embryonic stem cells. Lab Chip. 2008, 8:68-74; Leslie M (2011). News Focus: The power of One. Science, 331:24-26; Kalisky T, Quake S R (2011), Single cell genomics. Nat Methods. 8:311-4; Fritzsch F S (2012), Single-Cell Analysis in Biotechnology, Systems Biology, and Biocatalysis. Annu Rev ChemBiomol Eng.]. Additional methods for determining the levels of cAstr in a sample will be apparent to a person of skill in the art. In exemplary embodiments, automatic cell counting systems such as TC20™ Automated Cell Counter from BIO-RAD or SCEPTER™ 2.0 Handheld Automated Cell Counter from EMD Millipore may be used to determine the density of cAstr in a sample obtained from a subject.

In various embodiments of the processes, assays, systems and methods described herein, determining the density of cAstr also includes assaying the levels of the cell surface markers expressed on the surface of cAstr cells. Examples of cell markers for cAstr include but are not limited to glutamate-aspartate transporter (GLAST), brain lipid-binding protein (BLBP) and glial fibrillary acidic protein (GFAP). Determining the levels of the markers expressed comprises measuring the amount of marker proteins on cAstr present in the sample, or measuring the amount of nucleic acid encoding the marker proteins on cAstr present in the sample, or a combination thereof.

Assays for Detecting Mfsd2a

In various embodiments of the processes, assays, systems and methods described herein, determining the levels of Mfsd2a-containing cells comprises quantifying the cell-based biomarker in a sample obtained from the subject and/or the reference sample using manual or automated methods.

Any suitable immunoassay method may be utilized to quantify Mfsd2a-containing cells in a sample. Extensive discussion of the known immunoassay techniques is not required here since these are known to those of skill in the art. Typical suitable immunoassay techniques include sandwich enzyme-linked Immunoassay (ELISA), radioimmunoassay (RIA), competitive binding assay, homogeneous assay, heterogeneous assay, etc. Various known immunoassay methods are reviewed, e.g., in Methods in Enzymology, 70, pp. 30-70 and 166-198 (1980). In the assays of the invention, "sandwich-type" assay formats can be used. Some examples of the sandwich-type assays are described in by U.S. Pat. No. 4,168,146 to Grubb, et al. and U.S. Pat. No. 4,366,241 to Tom, et al. An alternative technique is the "competitive type" assay. In a competitive assay, the labeled probe is generally conjugated with a molecule that is identical to, or an analog of, the analyte. Thus, the labeled probe competes with the analyte of interest for the available receptive material. Examples of competitive immunoassay devices are described in U.S. Pat. No. 4,235,601 to Deutsch, et al., U.S. Pat. No. 4,442,204 to Liotta, and U.S. Pat. No. 5,208,535 to Buechler, et al.

In some embodiments of the processes, assays, systems and methods described herein, quantifying the level of Mfsd2a-containing cells includes contacting the sample from the patient with CNS disorder (such as BBB damage) with an antibody or a fragment thereof that specifically binds Mfsd2a, forming an antibody-protein complex between the antibody and Mfsd2a present in the sample, washing the sample to remove the unbound antibody, adding a detection antibody that is labeled and is reactive to the antibody bound to Mfsd2a in the sample, washing to remove the unbound labeled detection antibody and converting the label to a detectable signal, wherein the detectable signal is indicative of the level of Mfsd2a-containing cells in the sample from the patient. In some embodiments, the effector component is a detectable moiety selected from the group consisting of a fluorescent label, a radioactive compound, an enzyme, a substrate, an epitope tag, electron-dense reagent, biotin, digonigenin, hapten and a combination thereof. In some embodiments, the detection antibody is labeled by covalently linking to an enzyme, labeled with a fluorescent compound or metal, labeled with a chemiluminescent compound. The level of Mfsd2a-containing cells can be obtained by measuring a light scattering intensity resulting from the formation of an antibody-protein complex formed by a reaction of Mfsd2a in the sample with the antibody.

Antibodies, both polyclonal and monoclonal, can be produced by a skilled artisan either by themselves using well known methods or they can be manufactured by service providers who specialize making antibodies based on known protein sequences. For example, production of monoclonal antibodies can be performed using the traditional hybridoma method by first immunizing mice with an antigen which may be an isolated protein of choice or fragment thereof and making hybridoma cell lines that each produce a specific monoclonal antibody. The antibodies secreted by the different clones are then assayed for their ability to bind to the antigen using, e.g., ELISA or Antigen Microarray Assay, or immuno-dot blot techniques. The antibodies that are most specific for the detection of the protein of interest can be selected using routine methods and using the antigen used for immunization and other antigens as controls. The antibody that most specifically detects the desired antigen and protein and no other antigens or proteins are selected for the processes, assays and methods described herein. The best clones can be grown indefinitely in a suitable cell culture medium. They can also be injected into mice (in the peritoneal cavity, surrounding the gut) where they produce an antibody-rich ascites fluid from which the antibodies can be isolated and purified. The antibodies can be purified using techniques that are well known to one of ordinary skill in the art. In the present invention, the protein sequences are known and thus production of antibodies against them is a matter of routine.

The antibodies can be labeled. In some embodiments, the detection antibody is labeled by covalently linking to an enzyme, label with a fluorescent compound or metal, label with a chemiluminescent compound. For example, the detection antibody can be labeled with catalase and the conversion uses a colorimetric substrate composition comprises potassium iodide, hydrogen peroxide and sodium thiosulphate; the enzyme can be alcohol dehydrogenase and the conversion uses a coorimetric substrate composition comprises an alcohol, a pH indicator and a pH buffer, wherein the pH indicator is neutral red and the pH buffer is glycine-sodium hydroxide; the enzyme can also be hypoxanthine oxidase and the conversion uses a colorimetric substrate composition comprises xanthine, a tetrazolium salt and 4,5-dihydroxy-1,3-benzene disulphonic acid. In one embodiment, the detection antibody is labeled by covalently linking to an enzyme, label with a fluorescent compound or metal, or label with a chemiluminescent compound.

Direct and indirect labels can be used in immunoassays. A direct label can be defined as an entity, which in its natural state, is visible either to the naked eye or with the aid of an optical filter and/or applied stimulation, e.g., ultraviolet light, to promote fluorescence. Examples of colored labels which can be used include metallic sol particles, gold sol particles, dye sol particles, dyed latex particles or dyes encapsulated in liposomes. Other direct labels include radionuclides and fluorescent or luminescent moieties. Indirect labels such as enzymes can also be used according to the invention. Various enzymes are known for use as labels such as, for example, alkaline phosphatase, horseradish peroxidase, lysozyme, glucose-6-phosphate dehydrogenase, lactate dehydrogenase and urease. For a detailed discussion of enzymes in immunoassays see Engvall, Enzyme Immunoassay ELISA and EMIT, Methods of Enzymology, 70, 419-439 (1980).

The antibody can be attached to a surface. Examples of useful surfaces on which the antibody can be attached for the purposes of detecting the desired antigen include nitrocellulose, PVDF, polystyrene, and nylon. The surface or support may also be a porous support (see, e.g., U.S. Pat. No. 7,939,342). The assays can be carried out in various assay device formats including those described in U.S. Pat. Nos. 4,906,439; 5,051,237 and 5,147,609 to PB Diagnostic Systems, Inc.

A two-tailed student t-test with unequal variation may be used to measure the differences between a patient's expression of Mfsd2a-containing cells, and a normal blood sample, or the patient's own blood (matched control), or a reference generated by computer algorithm pooling many control samples, as described herein. A significant difference may be achieved where the p value is equal to or less than 0.05.

Reference Value

In various embodiments of the processes, assays, systems and methods described herein, the reference value is based on the density of cAstr or the level of Mfsd2a, whichever is applicable. In an embodiment, the reference level is in a blood sample. In an embodiment, the reference level is in a peripheral blood sample. In some embodiments, the reference value is the mean or median level of cAstr in a population of subjects that do not have a CNS disorder. In additional embodiments, the reference value is the level of cAstr in a sample obtained from the subject at a different (for example, an earlier) time point, such as during diagnosis, before treatment, after treatment or a combination thereof. In some embodiments, the reference value is the mean or median level of Mfsd2a-containing cells in a population of subjects that do not have a CNS disorder. In additional embodiments, the reference value is the mean or median level of Mfsd2a-containing cells in a sample obtained from the subject at a different (for example, an earlier) time point, such as during diagnosis, before treatment, after treatment or a combination thereof.

In various embodiments, the density of cAstr in a subject (for example, subject with CNS disorder such as BBB damage) compared to the reference value is increased by at least or about 10%, 20%, 30%, 40%, 50%, 60%, 70%, 80%, 90% or 100%. In various embodiments, the density of cAstr in a subject (for example, subject with CNS disorder such as BBB damage) compared to the reference value is increased by at least or about 1-fold, 2-fold, 3-fold, 4-fold, 5-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold or more or a combination thereof.

In various embodiments, the level of Mfsd2a-containing cells in a subject (for example, subject with CNS disorder such as BBB damage) compared to the reference value is increased by at least or about 10%, 20%, 30%, 40%, 50%, 60%, 70%, 80%, 90% or 100%. In various embodiments, the level of Mfsd2a-containing cells in a subject (for example, subject with CNS disorder such as BBB damage) compared to the reference value is increased by at least or about 1-fold, 2-fold, 3-fold, 4-fold, 5-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold or a combination thereof.

Therapies

As described herein, in exemplary embodiments, the NVU or BBB damage may be due to diseases including but not limited to hypertension, meningitis, traumatic brain injury, brain abscess, epilepsy, multiple sclerosis, neuromyelitisoptica, late-stage neurological trypanosomiasis, progressive multifocal leukoencephalopathy, de vivo disease and/or Alzheimer's diseases. Damage to the blood-brain barrier may also be caused by microbial infections, stroke, abused drugs and/or other pathogenic insults.

cAstr and/or cBMEC may be used as biomarkers for therapeutic responses. The transient disruption of the BBB has been used as a new approach for efficient delivery of various alkylglycerols into the CNS [Patel M M (2009), Getting into the brain: approaches to enhance brain drug delivery. CNS Drugs. 23:35-58]. The optimal degree of the BBB disruption is essential in monitoring the therapeutic response to those drugs. It can be easily indicated by quantification of cAstr or cBMEC, which can provide genome-wide profiling of BBB's cellular components, overcoming the limitation of MRI and the inability of molecular imaging agents to cross the BBB [Lelyveld V S (2010), Int J Imaging Syst Technol. 20:71-79]. cAstr/cBMEC can be also used as biomarkers for identification or validation of new CNS drug targets and for guiding the optimal dosing of drugs. Examination of cAstr and/or cBMEC may result in the identification and validation of drug targets specific for the CNS disorders that can cross the BBB without damaging the brain microvasculature. Defining the optimum dosage and schedule for CNS drugs has proven to be a challenge. It is increasingly recognized that the recommended dose for further exploration of a drug should be the optimal biological drug dose (OBD) rather than the maximum tolerated dose. Changes in cAstr and/or cBMEC counts after dose escalation may provide useful insights in establishing the OBD when assessing agents affecting the BBB. EPC may have great potential for use as a cellular therapy for enhancing vascular repair of BBB disorders because EPC are a population of rare cells that circulate in the blood with the ability to differentiate into BMEC.

In some embodiments, if a subject has increased likelihood of BBB damage, the therapeutic dosage may be adjusted, as would be apparent to a person of skill in the art. For example, if BBB damage is due to a bacterial or viral infection, the prescribed therapeutic dosage may be increased or decreased so as to reduce and/or inhibit damage to the BBB.

In some embodiments, if a subject has increased likelihood of BBB damage, a Src-inhibitor or nonspecific Src family kinase inhibitor (PP2) may be administered immediately optionally after thrombin injections to block brain edema and BBB disruption (for example, see Liu et al. Blood-brain barrier breakdown and repair by Src after thrombin—induced injury, Ann Neurol. 2010 April; 67(4): 526-33; Paul et al. Src deficiency or blockade of Src activity in mice provides cerebral protection following stroke, Nat Med. 2001 February; 7(2):222-7).

In some embodiments, if a subject has increased likelihood of BBB damage corticosteroids and glucocorticoids such as cortisone, hydrocortisone, prednisone, prednisolone, methylprednisolone, dexamethasone, betamethasone, triamcinolone, beclometasone, fludrocortisone acetate, deoxycorticosterone acetate (DOCA), aldosterone; glucocorticoid receptor agonist, and glucocorticoid receptor ligand may be administered to the subject (for example, see Fraser, "Can a broken barrier be repaired?" J Physiol. 2006 Jun. 1; 573(Pt 2): 287).

In some embodiments, if a subject has increased likelihood of BBB damage, Na—K—Cl cotransporter inhibitor such as bumetanide may be administered to the subject (for example, see, O'Donnell et al. Bumetanide inhibition of the blood-brain barrier Na—K—Cl cotransporter reduces edema formation in the rat middle cerebral artery occlusion model of stroke, J Cereb Blood Flow Metab. 2004 September; 24(9):1046-56).

EXAMPLES

The following examples are not intended to limit the scope of the claims to the invention, but are rather intended to be exemplary of certain embodiments. Any variations in the exemplified methods which occur to the skilled artisan are intended to fall within the scope of the present invention.

Chemicals and Reagent

Nicotine tartrate (NT) and methamphetamine (METH) were purchased from Sigma-Aldrich (St. Louis, Mo.). Dynabeads® M-450 Tosylactivated was obtained from Invitrogen (Carlsbad, Calif.) and utilized for magnetic bead extraction. Ulexeuropaeus 1 (UEA I) lectin and mounting medium with 4',6-diamidino-2-phenylindole (DAPI) were purchased from Vector (Buringame, Calif.). HIV-1 gp120 was purchased from Immunodiagnostics (Woburn, Mass.). Serum levels of molecular markers were determined by ELISA using antibodies and antigens from Creative Biomart (New York, N.Y.) (S100B) and ProteinTech (Chicago, Ill.) (ubiquitin C-terminal hydrolase 1, UCHL1). The Mfsd 2a antibody was purchased from Santa Cruz Biotechnology, Inc. (Dallas, TEXAS). All primary antibodies (Ab) were purchased from the commercial sources: a rabbit anti-α7 nAChR Ab from Genescript (Piscataway, N.J.); a rat anti-mouse Ly-6G (Gr-I) Ab; a mouse anti-CD44 Ab (sc-7297), a rabbit anti-actin (sc-7210), and a rabbit anti-GLUT1 Ab from Santa Cruz Biotechnology (Santa Cruz, Calif.); a rat anti-mouse Ly-6G (Gr-I) Ab FITC-conjugated and an anti-mouse CD146 Ab FITC-conjugated from eBiosciences (San Diego, Calif.), a rabbit anti-SIOOB Ab rhodamine-conjugated from BD Biosciences, and a rabbit anti-CD133 Ab rhodamine-conjugated from Abbiotec (San Diego, Calif.). Transwell filters (3 μm pore size, 6.5 mm diameter), blood plates and CBA assay kit were purchased from BD Biosciences (San Jose, Calif.). Chemicals were purchased from Sigma-Aldrich (St. Louis, Mo.) unless otherwise noted.

Animal Model and Treatment Protocol

All animal experiments were performed using C57BL/6J and gp120 transgenic mice. Heterozygous (+/−) α7-deficient mice with the C57BL/6J background (B6.129S7-Chrna$^{7tm1Bay}$/J) were purchased from Jackson Laboratory (Bar Harbor, Me.). Genotypes of α7$^{+/+}$ mice (WT mice), α7$^{−/−}$ mice (KO mice) and heterozygous α7$^{−/−}$ mice were determined according to the PCR protocol provided by the vendor. The animals were used in transgenic breeding at 8 weeks of age for optimum reproductive performance. The average litter size for neonatal mice was 10-15 days. Age and sex matched mice were used in all experiments. Three experiments were carried out. For meningitis mice model, C57BL/6J mice (6-8 days-old) were divided into 2 groups (I: Control treated with PBS; II: treated with E44) (n=4). All mice received E. coli K1 strain E44 (2×105 CFU) by intraperitoneal injection. Eighteen hours after E. coli inoculation, the animals were anaesthetized with ketamine and lidocaine, and blood samples were collected from heart puncture for bacterial culture using sheep blood plates. After perfusion from heart puncture with 20 ml PBS, the skull was opened. Brain tissue and CSF samples were collected as described previously. For NeuroAIDS mice model, C57BL/6Jmice (2 month-old) were treated as control with PBS (III); IV: gp120 transgenic mice treated with gp41 (n=4). The animals in Group IV received daily injections from tail veins (about 10 mg/Kg mouse wt.) of endotoxin-free recombinant HIV-1gp41 for 2 days as described previously. Then the blood samples were collected from heart puncture for bacterial culture using sheep blood plates. The brain tissue and CSF samples were collected as described above.

Isolation and Counting of Mouse cBMECs

Mouse cBMECs were isolated with Ulexeuropaeus 1 (UEA 1) lectin-coated Dynabeads as known by one of ordinary skill in the art. The beads were prepared according to the manufacturer's instructions (Invitrogen) and re-suspended in Hanks' balanced salt solution (HBSS. Invitrogen Corp., Carlsbad, Calif., USA) plus 5% fetal calf serum (HBSS+5% FCS) to a final concentration of 4×10$^8$ beads/mi. Mouse cBMECs in whole blood were affinity captured at 4TC with UEA UEA-1 coated Dynabeads. To eliminate non-specific cell binding to the beads, the cell suspensions were flushed through the pipette tip during the washing steps and then suspended in PBS by using a magnetic particle concentrator (MPC). The bound cells were incubated with 0.5M fucose for 10 min at room temperature to release the beads from target cells. The beads were then washed 5 times with HBSS+5% FBS and collected with the MPC. Then the suspensions were collected and centrifuged. The pellet was collected and affinity captured at 4-C with Msd2a-precoated Dynabeads. After blocking and washing, the cells conjugated to the beads were fixed with 2% paraformaldehyde and 0.25% glutaradehyde for 30 minutes. Then the FITC-conjugated CD146 antibody (BMECs specific marker, used for cBMEC identification) was added and incubated with the beads-bound cells overnight (dark). At last, DAPI was added and incubated with the beads-bound cells for 30 min. The cells (10 ul) were transferred to the cell counter, and counted under a florescence microscope.

Isolation and Counting of Astrocytes

Mouse astrocytes were isolated with Concanavalin A (ConA)-coated magnetic beads as known by one of ordinary skill in the art. Dynabeads™ beads were prepared according to the manufacturer's instructions (Invitrogen) and re-suspended in Hanks' balanced salt solution (HBSS, Invitrogen Corp., Carlsbad, Calif., USA) plus 5% fetal calf serum (HBSS+5% FCS) to a final concentration of 4×10$^8$ beads/ml. Mouse astrocytes in whole blood were affinity captured at 4° C. with ConA coated Dynabeads™. To eliminate non-specific cell binding to the beads, the cell suspensions were flushed through the pipette tip during the washing steps and then suspended in PBS by using a magnetic particle concentrator (MPC). The bound cells were incubated with 0.5M fucose for 10 min at room temperature to release the beads from target cells. The beads were then washed 5 times with HBSS+5% FBS and collected with the MPC. Then the suspensions were collected and centrifuged. The pellet was collected and affinity captured at 4° C. with ConA Dynabeads™. After blocking and washing, the cells conjugated to the beads were fixed with 2% paraformaldehyde and 0.25% glutaradehyde for 30 minutes. Then the FITC-conjugated GLAST antibody was added and incubated with the beads-bound cells overnight (dark). The cells (10 ul) were transferred to the cell counter, and counted under a florescence microscope.

Statistical Analysis

For the analysis of the in vitro data, ANOVA and covariates followed by a multiple comparison test such as the Newmann-Keuls test were used to determine the statistical significance between the control and treatment groups. Software GraphPadPrsim 5.0 was used for analysis of data from animal experiments. $P<0.05$ was considered to be significant.

Data were presented as mean±standard deviation. With the number of respective experiment run in triplicate, Categorical variables were compared byt test. Software GraphPad Prism 5.0 was used for analysis of data from the experiments. $P<0.05$ was considered to be significant.

Database

The protein access codes in Swissprot database are listed as follows: α7 nAChR, Mus muscularus, Q9JHD6; CD31, Mus muscularus, Q08481; CD34, Mus muscularus, Q64314; CD45, Mus muscularus, P06800; CD146, Mus muscularus, Q8R2Y2; S100B, Mus muscularus, P50114; UCHL1, Mus muscularus, P09936.

Transwell Assays of cBMEC Shedding

To further investigate cBMEC shedding, the double-chamber Transwell-based in vitro BBB model has been used. BMECs were isolated from WT and α7 nAChR KO mice as described in our recent publication. BMECs were cultured on collagen-coated Transwell polycarbonate tissue-culture inserts with a pore diameter of 12 μm (Coming Costar) for 5 days. BMECs were polarized and exhibited a trans-endothelial electrical resistance (TEER) of 200-250 Q cm$^2$, as measured with an Endohm volt/ohm meter in conjunction with an Endohm chamber (World Precision Instruments) as described previously. After exposure of the BMEC monolayer in the upper chamber to low doses of METH (10 nM), NT (10 µM), gp120 (50 ng/ml) and METH (10 nM)+gp120 (50 ng/ml) for 36 h, the shed cBMECs in the lower chambers were counted under the microscope. Simultaneously, the integrity of the BMEC monolayer was assessed by measurement of the TEER. Three measurements were made at each time-point for each sample.

Immunoblotting Assays for Mfsd2a Analyses

Western blotting was performed to determine the protein expression level of Mfsd2a in HBMECs, mouse brains and CSF, or clinical CSF samples. Brains were suspended in the lysate buffer (Cell Signaling Technology, Inc., Beverly, Mass.) containing 1% protease inhibitor Cocktail (Sigma-Aldrich), and then centrifuged at 12,000×g for 15 min at 4° C. All the protein fractions were stored at −80° C. until use and the protein concentrations were determined by Bio-Rad protein assay (Bio-Rad Laboratories, Hercules, Calif.) with bovine serum albumin as a standard. Proteins were separated by Novex 10% Trisglycine gel (Invitrogen, Carlsbad, Calif.) in SDSPAGE and the products were electro transferred onto nitrocellulose membranes. Membranes were then blocked with 1% BSA in Tris Buffer Saline+Tween (TBST) containing 0.1% Tween 20 for 1 h, and the blots were incubated with or rabbit anti-β-actin antibody (1:10000) at 4° C. overnight. Antibody incubations were performed in Blocker® BLOTTO in TBS (Pierce, Rockford, Ill.), a proprietary non-fat milk solution for blocking excessive binding in ELISA. The washed membranes were incubated with a horseradish peroxidase (HRP)-conjugated secondary antibody (rabbit anti-mice-rabbit IgG) for 1 h, and then the protein bands were visualized using an enhanced chemiluminescence procedure according to the manufacturer's instructions (Roche Applied Science, Indianapolis, Ind.) after the membrane was washed three times. Western blots were repeated at least three times for each sample. The relative amount of Mfsd2a was analyzed by a scanner using Quantity One® (Version4.6.2, Bio-Rad Laboratories, Hercules, USA) imaging system and represented as volume (intensity/mm2). The level of β-actin (Cell Signaling Technology, Inc.) was used to normalize for mouse brain samples loading, so the Mfsd2a of brain was quantified by the level of Mfsd2a/level of β-actin.

Example 1

Mfsd2a is required for the establishment of a functional BBB. The in vivo results show that Mfsd2a levels increased significantly in the brains of the *E. coli* or HIV-1 gp41 mouse model (FIG. 1). The results show that the mean of Mfsd2a protein levels in meningitis mouse brain is remarkably higher (1.88±0.26) than that in healthy controls (0.042±0.015, P=0.0062). The mean of Mfsd2a protein levels in the brain of mice treated with gp41 (1.62±0.21) were also higher than that in healthy controls (0.044±0.017, P=0.0032).

Example 2

Figure 2:
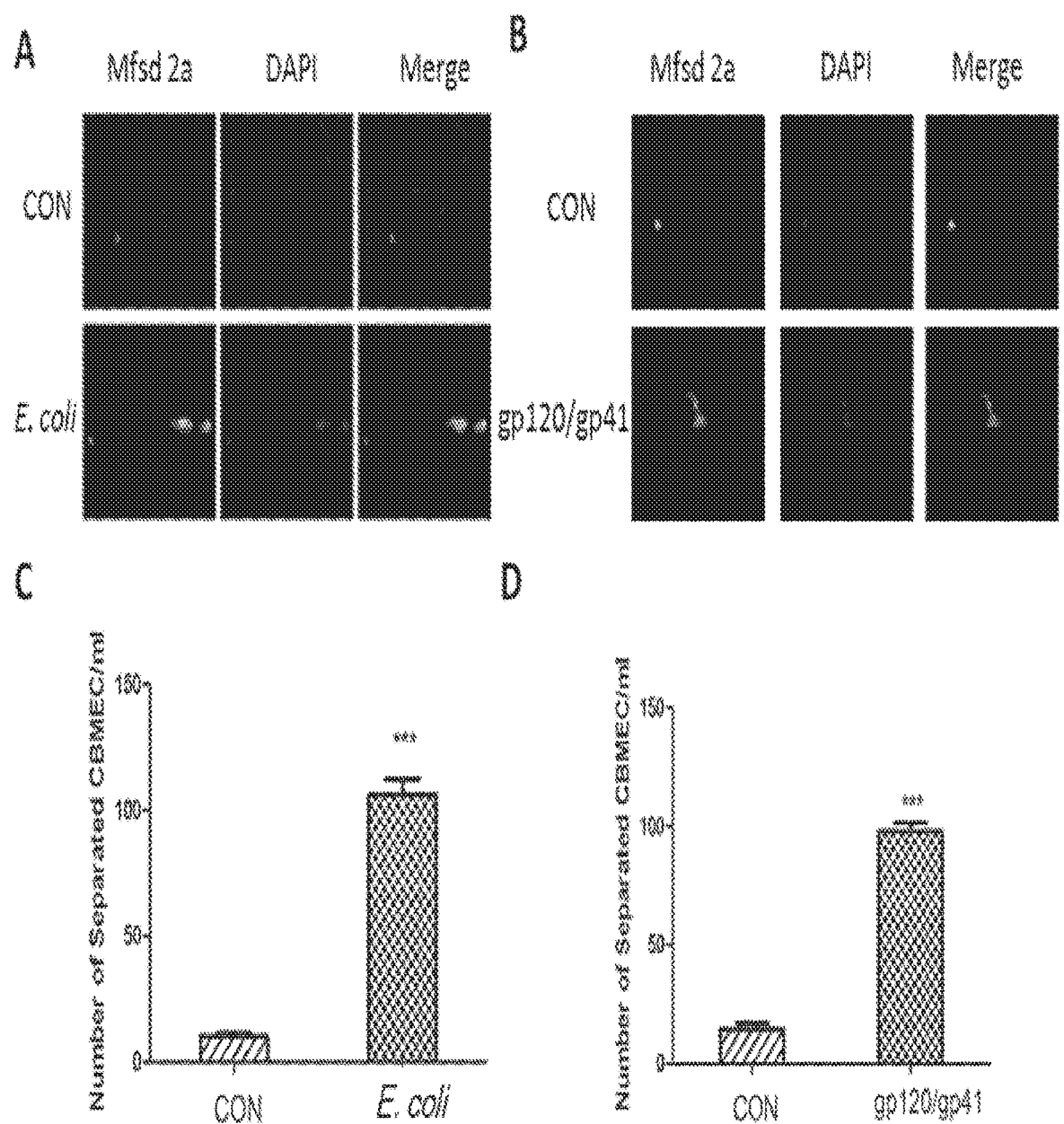
FIG. 2 demonstrates an increase in cBMEC shedding from BBB in the peripheral blood of mouse model treated with *E. Coli* or gp120/gp41. Mice treated with PBS is used as control. The cBMECs from the whole peripheral blood of mice is isolated and harvested via the use of UEA magnetic beads. Double staining was done using DAPI (blue color) and antibodies against CD146 (green color) (specific for ECs). Significantly more cBMECs are detected in the peripheral blood samples from mice treated with *E. coli* (A, C) and gp120 (B, D). CON, Control (***P<0.001). n=3 litters (3 biological replicates).

In order to determine whether cBMECs are present in the peripheral blood of a subject that has suffered microbial insults, UEA-1 coated beads was used to quantify the number of cBMECs in the mice peripheral blood. Total cBMECs (Mfsd2a+/DAPI+) were identified based on another specific proteins CD146 (FIG. 2). Our studies confirm that very small numbers of cBMECs (10.0±1.29/ml) could be isolated from the peripheral blood and that significant changes in the levels of cBMECs captured by the anti-Mfsd2a antibody GLAST in the peripheral blood streams in the animals treated with *E. coli* and HIV virulence factors. Remarkably, Mfsd2a+cBMECs were increased in mice treated with *E. coli* (106.3±6.3/ml) and gp41-treated mice (98.0±3.5/ml) (P<0.001) (FIG. 2).

Example 3

Figure 3:
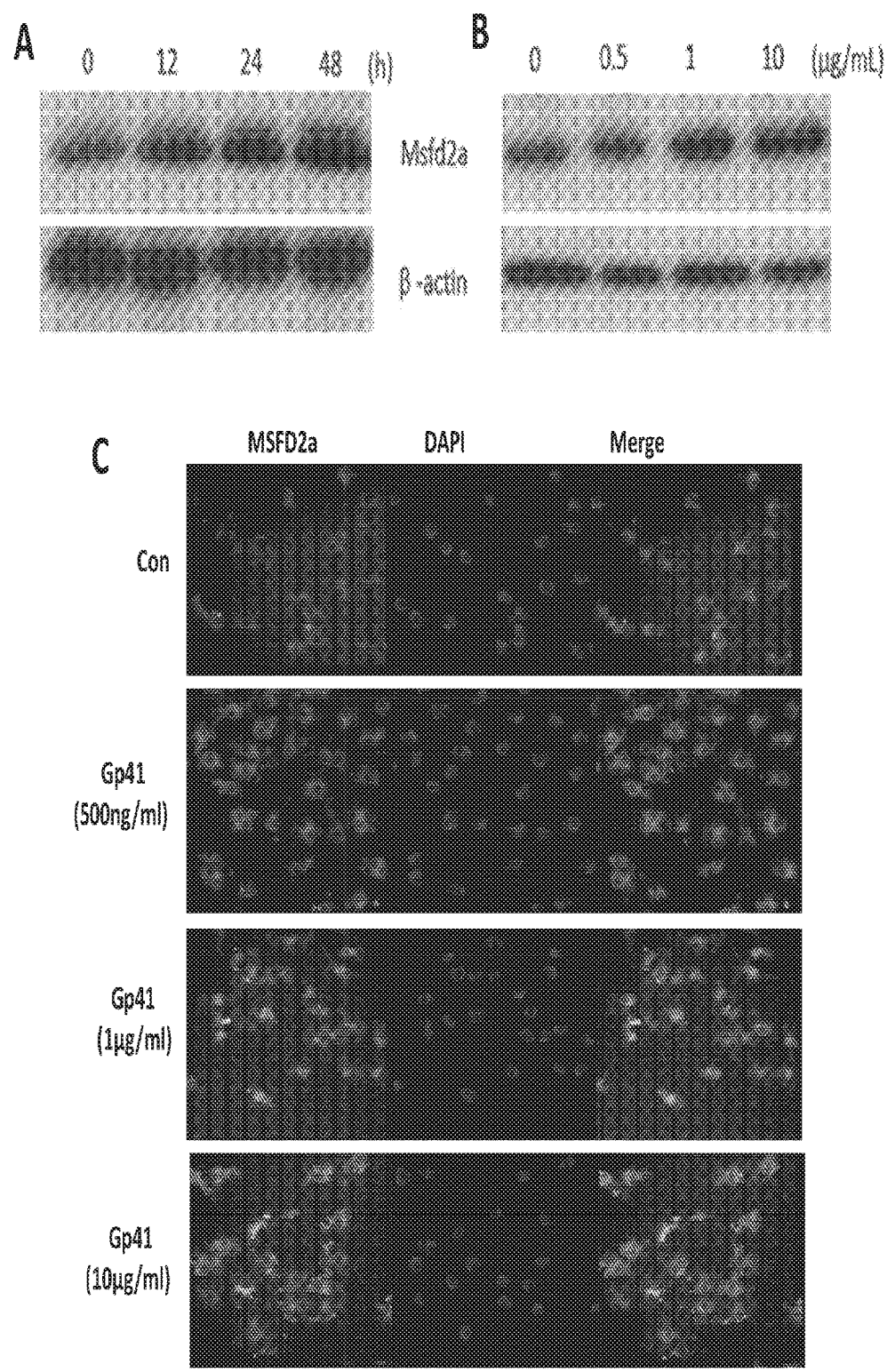
FIG. 3 demonstrates increased expression of Mfsd2a in Human Brain Microvascular Endothelial Cells (HBMEC) treated with gp41. The level of Mfsd2a is shown by western blotting analysis for different time points of treatment with 1 μg of gp41 (A) and for different doses of gp41 (B). Immunofluorescence microscopy analysis of Mfsd2a expression in HBMECs was performed (C). Immunofluorescence microscopic images were obtained using anti-Mfsd2a antibody (green) and nuclear DNA staining dye DAPI (blue). (C1: Con) Mfsd2a expression of HBMECs without being treated gp41. (C2) Mfsd2a expression of HBMECs treated with 500 ng/mL of gp41. (C3) Mfsd2a expression of HBMECs treated with 1 μg/mL of gp41. (C4) Mfsd2a expression of HBMECs treated with 10 μg/mL of gp41.

This set of experiments attempt to determine whether the level of Mfsd2a increases in HBMEC upon treatment of gp41. The western blotting results show that gp41-increased Mfsd2a protein levels in HBMEC are time- and dose-dependent (FIG. 3A-C). The western blotting results show that the Mfsd2a protein levels in HBMEC treated with gp41 are significantly higher than those in the controls without treatment.

Example 4

Figure 4:
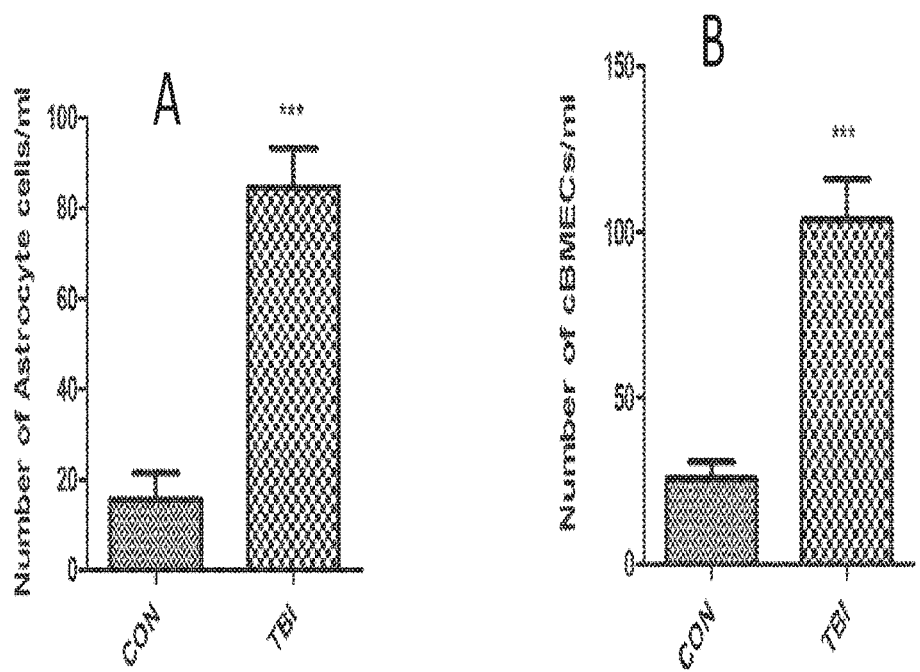
FIG. 4 demonstrates the density of cAstr (A) and cBMEC (B) cells in the peripheral blood samples of patients suffering traumatic brain injury (TBI) are significantly higher than control samples. Bars denote mean values, and error bars describe SEM. p<0.05; *P<0.01.

To determine the clinical feasibility of the cell-based biomarker assays for TBI, the preliminary studies on the detection and enumeration of cAstr and cBMEC in the peripheral blood samples of TBI patients and age-matched controls were carried out with the institutional approval. The assays were performed. As shown in the studies, blood levels of cAstr and cBMEC were significantly higher (P<0.001) in the TBI patients as compared with the age-matched controls (FIG. 4).

Example 5

Figure 5:
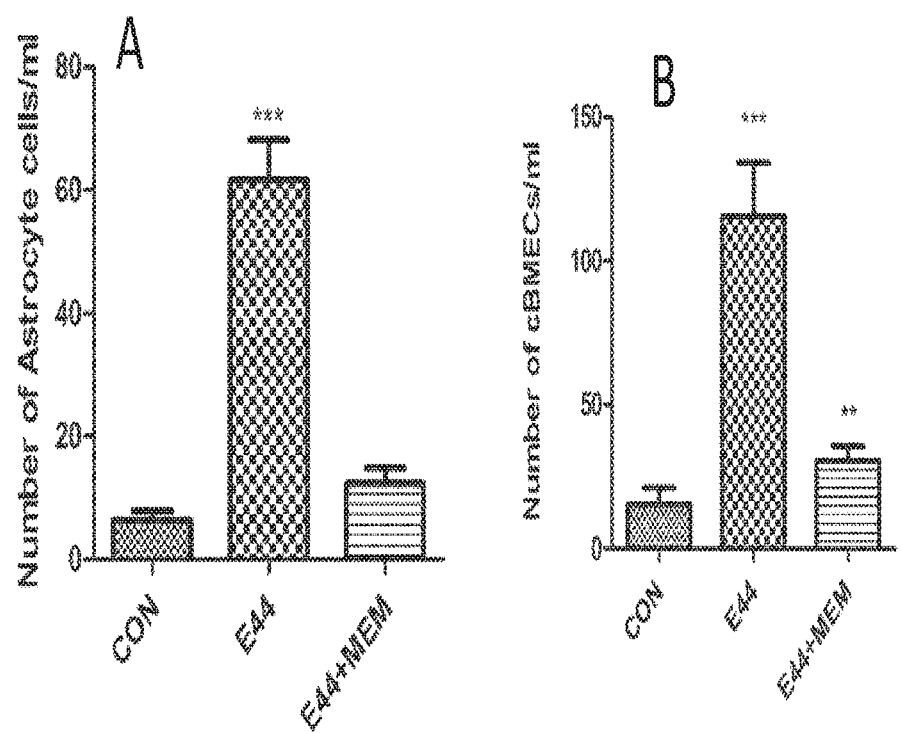
FIG. 5 depicts the effects of memantine (MEM) on *E. coli* E44-induced increase of cAstr (A) and cBMEC (B) cell density in the peripheral blood of mice. MEM mediates chemical blockage of α7 nAChR receptor. Bars denote mean values, and error bars describe SEM. p<0.01; *P<0.001.

As α7 nAChR plays an important role in CNS Inflammation induced by microbial and non-microbial factors, we have proposed that turnover and shedding of astrocytes and BMECs could be regulated by α7 nAChR. To test this hypothesis, the correlation of α7 nAChR with cAstr/cBMEC shedding and CNS inflammation induced by meningitic *E. coli* K1 (E44) was examined an α7 nAChR antagonist memantine (MEM) described in the experimental methods herein. In this study, neonatal (10 day-old) mice were intraperitoneally injected with E44 and treated with MEM. As shown in FIG. 5, MEM could significantly block shedding of both cAstr (5A) and cBMECs (5B) (P<0.001), suggesting that α7 nAChR plays an essential role in the pathogenic effects of E44 on the BBB.

Example 6

Figure 6:
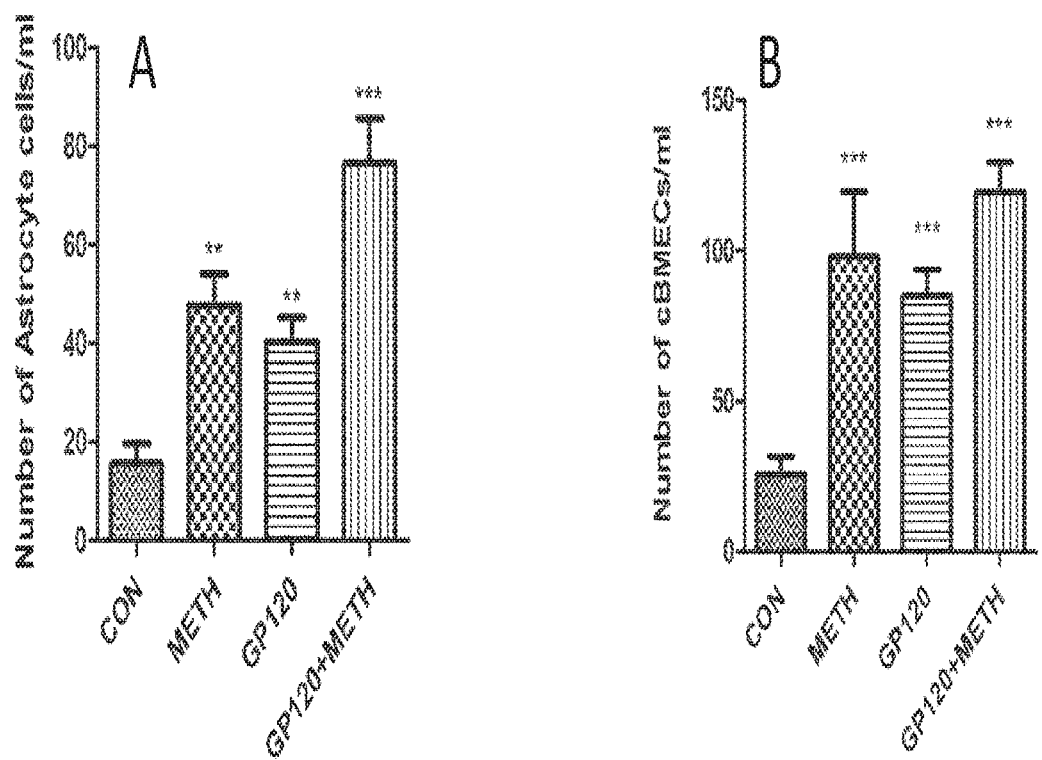
FIG. 6 depicts the effects of gp120 or methamphetamine on the density of cAstr (A) and cBMEC (B) cells in the peripheral blood of mice treated with gp120 and METH. Bars denote mean values, and error bars describe SEM. p<0.01; *P<0.001.

This set of experiments are designed to determine if cAstr and cBMECs can be detected and be used as a cellular index of the BBB damage caused by microbial (gp120) and non-microbial (METH) pathogenic insults. As seen in FIGS. 6A & 6B, METH and gp120 could significantly induce Astr (6A) and cBMEC (6B) shedding than the controls without treatment (CON). Moreover, significantly higher levels of Astr and cBMECs are detected in the combination of gp120 with METH.

We have developed a new model for the discovery of cell-based BBB biomarkers. Our studies have suggested for the first time that cAstr/cBMECs can be detected and be used as a cellular Index of the BBB damage caused by microbial (*E. coli* K1 and gp120) and non-microbial (nicotine and METH) pathogenic insults. The inflammatory response may be regulated by α7 nAChR. It has been a very challenging issue to directly make the quantification of the NVU or BBB injury caused by various pathogenic insults. Most biomarker research into CNS disorders has focused on neuronal damage not on NVU or BBB injury, because neuronal sensitivity to certain pathogenic insults is region- and disease-specific. Therefore, much previous research on brain injury has focused on biomarkers that measure neuronal damage. There are a number of clinical advantages for shifting the focus on NVU or BBB injury. Firstly, most CNS diseases are accompanied by increased NVU or BBB dysfunction. Secondly NVU or BBB injury does occur concomitantly with the pathogenic insult, but neuronal damage may develop slowly or after a delay. The early detection of NVU or BBB disorders offers a window opportunity for neuroprotective intervention. Another advantage is that the cell-based biomarkers cAstr/cBMECs along with the single cell profiling (SCP) approaches will make the diagnosis of CNS disorders much easier and acceptable. Recent advances in biotechnologies for proteomic and genomic analysis at single-cell resolution enable a global novel understanding of complex biological processes. The SCP approaches will allow the study of multiple genes/proteins or entire genomes/proteomes of cAstr and/or cBMECs. Considering these advantages, the current studies are primarily designed to lay foundations for the use of cAstr/cBMECs as cellular biomarkers of the NVU or BBB injury, which contributes to various CNS disorders. In the current report, we demonstrated that cAstr/cBMECs could be used as cell-based biomarkers for NVU or BBB disorders caused by microbial (e.g., gp120 and meningitic $E.$ $coli$ K1) and non-microbial (e.g., nicotine and METH) factors.

Our previous studies demonstrated that both microbial (e.g., $E.$ $coli$ K1) and non-microbial (e.g., nicotine) factors could up-regulate α7 nAChR and that CNS inflammation induced by these pathogenic insults could be blocked by α7 antagonist-mediated inhibition and genetic knockout of the α7 gene. In concurrence with these findings, α7 nAChR could be up-regulated by METH and gp120, which are involved in the pathogenesis of HIV-associated neurocognitive disorder (HAND). In this report, we have established that α7 nAChR plays an important role in regulation of BBB integrity in the mouse model. The pathogenic insult-induced cAstr/cBMEC shedding, which is correlated with increased BBB permeability, is significantly reduced in the α7-deficient mice. These data suggest that up-regulation of α7 nAChR is detrimental to the NVU and BBB integrity and function.

The precise mechanism responsible for the pathogenic insult-mediated increase in BBB permeability and cAstr/cBMEC shedding during CNS inflammation is unknown. Although it is well-known that pro-inflammatory factors promote increased BBB permeability, it is unclear how the production of these factors is regulated during CNS disorders. Our previous studies showed that α7 nAChR could directly or indirectly upregulate pro-inflammatory factors (IL-1, IL-6, TNFa, MCP-1, MIP-1a, RANTES, CD44 and ICAM-1), significantly enhance PMN transmigration into CSF and has a detrimental effect on the permeability of the BBB in the early stages of meningitic infection. Calcium signaling mediated by α7 nAChR is the major regulatory pathway for the CNS inflammatory response to meningitic $E.$ $coli$ infection and nicotine exposure. Using the α7 KO mouse model, we demonstrated that decreased cAstr/cBMEC shedding was correlated with CNS inflammatory response (e.g., decreased PMN recruitment and albumin leakage into CSF) when compared to that in the wildtype animals. These findings provide insight into an element of host defense previously unknown to contribute to the NVU/BBB integrity and cAstr/cBMEC shedding, but the implications of the cholinergic α7 nAChR pathway for the pathogenesis and therapeutics of BBB disorders and CNS inflammation remain to be explored. Alpha7 nAChR has been found to be able to mediate SLURP (secreted mammalian Ly-6/urokinase plasminogen activator receptor-related protein)-1-upregulated NF-KB through both ionic events (calcium signaling) and activation of protein kinases. Both UCHL1 and S1OOB are shown to be involved in regulation of NF-KB. It is likely that α7 nAChR-mediated NF-KB signaling may be involved in regulation of both the molecular (UCHL1 and S100B) and cellular (cAstr/cBMEC shedding) biomarkers during various CNS disorders.

In conclusion, the blood levels of cAstr and cBMECs, as well as EPCs positively correlate with NVU or BBB injury and host inflammatory response during CNS inflammation induced by microbial and non-microbial factors. These results enlighten the potential of these noninvasive cell-based biomarkers in indexing NVU or BBB injury and optimize therapeutic options.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

REFERENCES

Zhen Zhao, et al., Establishment and Dysfunction of the Blood-Brain Barrier. Cell, 163: 1064-78, 2015.

Johansson B B. Hypertension mechanisms causing stroke. ClinExpPharmacol Physiol. 26:563-5, 1999.

CDC High Blood Pressure Fact Sheet. 2016. https://www.cdc.gov/dhdsp/data_statistics/fact_sheets/fs_blood-pressure.htm.

Huang S H, Zhang B, Zhou Y H. Why Molecular Biomarkers of Traumatic Brain Injury May Never Work: Effects of Glymphatic Pathway Dysfunction. J Trauma Treatment, 5:2, 2016.

Yu J Y, Zhang B, Peng L, Wu C H, Cao H, Zhong J F, Hoffman J, Huang S H. Repositioning of memantine as a potential novel therapeutic agent against meningitic *E. coli*-induced pathogenicities through disease-associated alpha7 cholinergic pathway and RNA sequencing-based transcriptome analysis of host inflammatory responses. PLoS One. 2015, 10:e0121911. PMID: 25993608.

Ben-Zvi A, Lacoste B, Kur E, Andreone B J, Mayshar Y, et al. (2014) Mfsd2a is critical for the formation and function of the blood-brain barrier. Nature 509:507-11.

Chernyavsky A I, Arredondo J, Galitovskiy V, Qian J, Grando S A. Upregulation of nuclear factor-kappaB expression by SLURP-1 is mediated by alpha7-nicotinic acetylcholine receptor and involves both ionic events and activation of protein kinases. Am J Physiol Cell Physiol. 2010, 299:C903-11.

Huang S H, Chi F, Wang L, Wu C H, Cao H, Zhang A M, Jong A: Circulating microvascular endothelial cells (cBMEC). as potential biomarkers of blood-brain barrier disorders caused by microbial and non-microbial factors. PLoS One. 2013, 8:e62164. (The first paper on the correlation of cell-based biomarkers with BBB disorders induced by HIV-1 virotoxins and other pathogenic insults). PMID: 23637989.

Patel M M, Goyal B R, Bhadada S V, Bhatt J S, Amin A F (2009) Getting into the brain: approaches to enhance brain drug delivery. CNS Drugs. 23: 35-58.

Begley D J (2006) Structure and Function of the Blood-brain barrier. In "Enhancement in Drug Delivery" (Ed. by E. Touitou & B W Barry). CRC Press, p. 575-589.

Manda K R, Banerjee A, Banks W A, Ercal N (2011) Highly active antiretroviral therapy drug combination induces oxidative stress and mitochondrial dysfunction in immortalized human blood-brain barrier endothelial cells. Free RadieBiol Med. 50: 801-10.

Lamers S L, Gray R R, Salemi M, Huysentruyt L C, McGrath M S (2011) HIV-I phylogenetic analysis shows HIV-I transits through the meninges to brain and peripheral tissues. Infect Genet Evol. 11: 31-7.

Strazza M, Pirrone V, Wigdahl B, Nonnemacher M R (2011) Breaking down the barrier: the effects of HIV-I on the blood-brain barrier. Brain Res. 1399: 96-115.

Friedman H, Newton C, Klein T W (2003) Microbial infections, immunomodulation, and drugs of abuse. ClinMicrobiol Rev. 16: 209-19.

Huang S H, Wass C A, Fu Q, Prasadarao N A, Stins M F, et al. (1995) *Escherichia coli* invasion of brain microvascular endothelial cells in vitro and in vivo: molecular cloning and characterization of invasion geneibelO, Infect. Immun. 63: 4470-4475.

Huang S H, Stins M F, Kim K S (2000) Bacterial penetration across the blood-brain barrier during the development of neonatal meningitis. Microbes and Infection 2: 1237-1244.

Stins M F, Shen Y, Huang S H, Gilles F, Kalra V K, et al. (2001) Gp120 activates children's brain endothelial cells via CD4. J. Neurovirol 7: 125-34.

Chen Y H, Chen H M, Zhou Z Y, Li W, Jong A Y, et al. (2002) Enhanced *Escherichia coli* invasion of human brain microvascular endothelial cells is associated with alterations in cytoskeleton induced by nicotine. Cell Microbiol. 4: 503-14.

Kim K S (2003) Pathogenesis of bacterial meningitis: from bacteraemia to neuronal injury. Nat Rev Neurosci 4: 376-385.

Jong A, Wu C H, Jiang S, Feng L, Chen H M, et al. (2007) HIV-I gp41 ectodomain enhances *Cryptococcus neoformans* binding to HBMEC. Biochem. Biophys. Res. Commun. 356: 899-905.

Jong A, Wu C H, Zhou W, Chen H M, Huang S H (2008) Infectomic analysis of gene expression profiles of human brain microvascular endothelial cells infected with *Cryptococcus neoformans*. J. Biomed. Biotechnol. (2008) 375620.

Chi F, Wang L, Zheng X Y, Wu C H, Jong A, et al. (2011) Meningitic *Escherichia coli* KI penetration and neutrophil transmigration across the blood-brain barrier are modulated by alpha7 nicotinic receptor. PLoS One. 6: e25016.

Chi F, Wang L, Zheng X, Jong A, Huang S H. Recruitment of 07 nicotinic acetylcholine receptor to caveolin-1-enriched lipid rafts is required for nicotine-enhanced *Escherichia coli* KI entry into brain endothelial cells. Future Microbiol 2011, 6: 953-66. PMID: 21861625.

Huang S H, Wu C H, Jiang S B, Bahner I, Lossinsky A S, et al. (2011) HIV-I gp41 ectodomain enhances *C. neoformans* binding to human brain microvascular endothelial cells via gp41 core-induced membrane activities. Biochem J. 438: 457-66.

Chi F, Bo T, Wu C H, Jong A, Huang S H (2012) Vimentin and PSF Act in Concert to Regulate IbeA+*E. coli* KI Induced Activation and Nuclear Translocation of NF-KB m Human Brain Endothelial Cells. PLoS One. 7: e35862.

Huang S H, Wu C H, Chang Y C, Kwon-Chung K J, Brown R J, et al. (2012) *Cryptococcus neoformans*-Derived Microvesicles Enhance the Pathogenesis of Fungal Brain Infection. PLoS One. 7: e48570.

Olsen A I, Morrey J D, Smee D F, Sidwell R W (2007) Correlation between breakdown of the blood-brain barrier and disease outcome of viral encephalitis in mice. Antiviral Res. 75: 104-112.

Lelyveld V S, Atanasijevic T, Jasanoff A (2010) Challenges for Molecular Neuroimaging with MRI. Int J Imaging Syst Technol. 20: 71-79.

Blann A D, Woywodt A, Bertolini F, Bull T M, Buyon J P. et al. (2005) Circulating endothelial cells: Biomarkers of vascular disease. ThrombHaemost. 93: 228-35.

Strijbos M H, Gratama J W, Kraan J, Lamers C H, den Bakker M A, et al. (2008) Circulating endothelial cells in oncology: pitfalls and promises. Br J Cancer 98: 1731-1735.

Haubitz M, Dhaygude A, Woywodt A (2009) Mechanisms and markers of vascular damage in ANCA-associated vasculitis. Autoimmunity 42: 605-14.

Kraan J, Sleijfer S, Foekens J A, Gratama J W (2012) Clinical value of circulating endothelial cell detection in oncology. Drug Discov Today 17: 710-7.

Goon P K, Lip G Y, Boos C J, Stonelake P S, Blann A D (2006) Circulating endothelial cells, endothelial progenitor cells, and endothelial microparticles in cancer. Neoplasia. 8: 79-88.

Bertolini F, Shaked Y, Mancuso P, Kerbel R S (2006) The multifaceted circulating endothelial cell in cancer: towards marker and target identification. Nat Rev Cancer 6: 835-45.

Foster W, Shantsila E, Carruthers D, Lip G Y, Blann A D (2009) Circulating endothelial cells and rheumatoid arthritis: relationship with plasma markers of endothelial damage/dysfunction. Rheumatology (Oxford) 48: 285-8.

Steiner J, Bernstein H G, Bielau H, Berndt A, Brisch R, et al. (2007) Evidence for a wide extra-astrocytic distribution of SIOOB in human brain. BMC Neurosci 8:2.

Liu L, Uu H, Jiao J, Uu H, Bergeron A, et al. (2007) Changes in circulating human endothelial progenitor cells after brain injury. J Neurotrauma 24: 936-43.

Bogoslovsky T, Chaudhry A, Latour L, Marie D, Luby M, et al. (2010) Endothelial progenitor cells correlate with lesion volume and growth in acute stroke. Neurology 75: 2059-62.

Zhang X, Winkles J A, Gongora M C, Polavarapu R, Michaelson J S, et al. (2007) TWEAK-Fn14 pathway inhibition protects the integrity of the neurovascular unit during cerebral ischemia. J Cereb Blood Flow Metab 27: 534-544.

Lee J D, Tsai L Y, Chen C H, Wang J J, Hsiao J K, et al. (2006) Blood-brain barrier dysfunction occurring in mice infected with Angiostrongyluscantonensis. Acts Trop 97: 204-11.

Miric O, Katanic R, Kisic B. Zoric L, Miric B, et al. (2010) Oxidative stress and myeloperoxidase activity during bacterial meningitis: effects of febrile episodes and the BBB permeability. Clin Biochem 43: 246-52.

Blyth B J, Farahvar A, He H, Nayak A, Yang C, et al. (2011) Elevated serum ubiquitin carboxy-terminal hydrolase LI is associated with abnormal blood-brain barrier function after traumatic brain injury. J Neurotrauma 28: 2453-62.

Jackson C J, Garbett P K, Nissen B, Schrieber L (1990) Binding of human endothelium to Ulexeuropaeus I-coated Dynabeads: application to the isolation of microvascular endothelium. J Cell Sci 96: 257-262.

Marchi N, Cavaglia M, Fazio V, Bhudia S, Hallene K, et al. (2004) Janigro D. Peripheral markers of blood-brain barrier damage. ClinChimActa. 342: 1-12.

Zhong J F, Chen Y, Marcus J S, Scherer A, Quake S R, et al. (2008) Taylor C R, Weiner L P. A microfluidic processor for gene expression profiling of single human embryonic stem cells. Lab Chip 8: 68-74.

Leslie M (2011) News Focus: The power of One. Science 331: 24-26.

Stahlberg A, Kubista M, Aman P (2011) Single-cell gene-expression profiling and its potential diagnostic applications. Expert Rev MolDiagn 11: 735-40.

Kalisky T, Quake S R (2011) Single cell genomics. Nat Methods 8: 311-4.

Fritzsch F S, Dusny C, Frick 0, Schmid A (2012) Single-Cell Analysis m Biotechnology, Systems Biology, and Biocatalysis. Annu Rev ChemBiomolEng 3: 129-55.

Jung K H, Roh J K (2008) Circulating Endothelial Progenitor Cells in Cerebrovascular Disease. J ClinNeurol 4: 139-147.

Fink K, Schwarz M, Feldbriigge L, Sunkomat J N, Schwab T, et al. (2010) Severe endothelial injury and subsequent repair in patients after successful cardiopulmonary resuscitation. Crit Care 14: R104.

Porto I, Leone A M, De Maria G L, Craig C H, Tritarelli A, et al. (2011) Are endothelial progenitor cells mobilized by myocardial ischemia or myocardial necrosis? A cardiac magnetic resonance study. Atherosclerosis 216: 355-8.

Rouhl R P W, van Oostenbrugge R J, Damoiseaux J G, Debrus-Palmans L L, Theunissen R O, et al. (2009) Haptoglobin phenotype may alter endothelial progenitor cell cluster formation in cerebral small vessel disease. CurrNeurovasc Res 6: 32-41.

Deanfield J E, Halcox J P, Rabelink T J (2007) Endothelial function and dysfunction: testing and clinical relevance. Circulation. 115: 1285-95.

Esteve-Rudd J, Campello L, Herrero M T, Cuenca N, Martin-Nieto J (2010) Expression in the mammalian retina of parkin and UCH-LI, two components of the ubiquitin-proteasome system. Brain Res 1352: 70-82.

Day I N, Thompson R J (2010) UCHL1 (PGP 9.5); neuronal biomarker and ubiquitin system protein. ProgNeurobiol. 90: 327-62.

Mitra S, Sammani S, Wang T, Boone D L, Meyer N J, et al. (2011) Role of growth arrest and DNA damage-inducible a in Akt phosphorylation and ubiquitination after mechanical stress-induced vascular injury. Am J Respir-Crit Care Med 184: 1030-40.

Zhong J, Zhao M, Ma Y, Luo Q, Liu J, Wang J, et al. (2012) UCHL1 acts as a colorectal cancer oncogene via activation of the -catenin/TCF pathway through its deubiquitinating activity. Int J Mol Med. 30: 430-6.

Sacco J J, Coulson J M, Clague M J, Urbe S (2010) Emerging roles of deubiquitinases in cancer-associated pathways. IUBMB Life. 62: 140-57.

Takami Y, Nakagami H, Morishita R, Katsuya T, Cui T X, et al. (2007) Ubiquitin carboxyl-terminal hydrolase LI, a novel deubiquitinating enzyme in the vasculature, attenuates NF-kappaBactivation. ArteriosclerThromb Vasc Biol 27: 2184-90.

Northrop N A, Smith L P, Yamamoto B K, Eyerman D J (2011) Regulation of glutamate release by α7 nicotinic receptors: differential role in methamphetamine-induced damage to dopaminergic and serotonergic terminals. J PharmacolExpTher 336: 900-7.

Pendyala G, Buescher J L, Fox H S (2012) Methamphetamine and inflammatory cytokines increase neuronal Na+/K+-ATPase isoform 3: relevance for HIV associated neurocognitive disorders. PLoS One. 7: e37604.

Ballester L Y, Capo-Velez C M, Garcia-Beltran W F, Ramos F M, Vazquez-Rosa E, et al. (2012) Up-regulation of the neuronal nicotinic receptor α7 by HIV glycoprotein 120: potential implications for HIV-associated neurocognitive disorder. J Biol Chem. 287: 3079-86.

Zhang Y, Wang M, Li H, Zhang H, Shi Y, Wei F, et al. (2012) Brain Res. Accumulation of nuclear and mitochondrial DNA damage in the frontal cortex cells of patients with HIV-associated neurocognitive disorders (I 458)1-11.

Slominski A (2010) Nicotinic receptor signaling in nonexcitable epithelial cells: paradigm shifting from ion current to kinase cascade. Focus on "Upregulation of nuclear factor-kappaB expression by SLURP-I is mediated by alpha7-nicotinic acetylcholine receptor and involves both ionic events and activation of protein kinases". Am J Physiol Cell Physiol. 299: C885-7.

Tsoporis J N, Izhar S, Proteau G, Slaughter G, Parker T G (2012) SIOOB-RAGE dependent VEGF secretion by cardiac myocytes induces myofibroblast proliferation. J Mol Cell Cardiol. 52: 464-73.

Matta S G, Balfour D J, Benowitz N L, Boyd R T Buccafusco J J, et al. (2006) Guidelines on nicotine dose selection for in vivo research. Psychopharmacology 190: 269-319. Martinez L R, Mihu M R, Gacser A, Santambrogio L. Nosanchuk J D (2009) Methamphetamine enhances histoplasmosis by immunosuppression of the host. J Infect Dis 200: 131-41.

Banerjee A, Zhang X, Manda K R, Banks W A, Ercal N (2010) HIV proteins (gp120 and Tat) and methamphetamine in oxidative stress-induced damage in the brain: potential role of the thiol antioxidant N-acetylcysteine amide. Free RadieBiol Med 48: 1388-98.

Loram L C, Harrison J A, Chao L, Taylor F R, Reddy A, et al. (2010) Intrathecal injection of an alpha seven nicotinic acetylcholine receptor agonist attenuates gp120-induced mechanical allodynia and spinal pro-inflammatory cytokine profiles in rats. Brain BehavImmun 24: 959-67.

Oh S K, Cruikshank W W, Raina J, Blanchard G C, Adler W H, et al. (1992) Identification of HIV-I envelope glycoprotein in the serum of AIDS and ARC patients. J Acquir Immune DeficSyndr 5: 251-6.

Fleming J O, Ting J Y, Stohlman S A, Weiner L P (1983) Improvements in obtaining and characterizing mouse cerebrospinal fluid. Application to mouse hepatitis virus-induced encephalomyelitis. J Neuroimmunol 4: 129-140.

Che X, Chi F, Wang L, Jong T D, Wu C H, et al. (2010) Involvement of IbeA in meningitic *Escherichia coli* KI-induced polymorphonuclear leukocyte transmigration across brain endothelial cells. Brain Pathology 21: 389-404.

Stastny F, Dvorakova L, Lisy V (1997) Biochemical characteristics of gamma-glutamyltranspeptidase in capillaries from entorhinohippocampal complex of quinolinate lesioned rat brain. MolChemNeuropathol. 32: 143-61.

Nakagawa S, Deli M A, Kawaguchi H, Shimizudani T, Shimono T, et al. (2009) A new blood-brain barrier model using primary rat brain endothelial cells, pericytes and astrocytes. NeurochemInt 54: 253-263.

Chen S H, Stins M F, Huang S H, Chen Y H, Kwon-Chung K J, et al. (2003) *Cryptococcus neoformans* induces alterations in the cytoskeleton of human brain microvascular endothelial cells. J Med Microbiol 52: 961-70.

Mahajan S D, Aalinkeel R, Sykes D E, Reynolds J L, Bindukumar B, et al. (2008) Methamphetamine alters blood brain barrier permeability via the modulation of tight junction expression: Implication for HIV-I neuropathogenesis in the context of drug abuse. Brain Res 1203: 133-48.

Chi F, Jong T D, Wang L, Ouyang Y, Wu C H, Li W. Huang S H. Vimentin-mediated signaling is required for IbeA+*E. coli* KI invasion of human brain microvascular endothelial cells. Biochem J. 2010, 427:79-90.

Moriwaki Y, Watanabe Y, Shinagawa T, Kai M, Miyazawa M, Okuda T, Kawashima K, Yabashi A, Waguri S, Misawa H. Primary sensory neuronal expression of SLURP-I, an endogenous nicotinic acetylcholine receptor ligand. Neurosci Res. 2009, 64:403-12.

The invention claimed is:

1. A method for diagnosing a traumatic brain injury, the method comprising:
   (a) obtaining a peripheral blood sample from a human subject;
   (b) concentrating circulating brain microvascular endothelial cells from the peripheral blood sample sequentially by using a plurality of lectin coated magnetic beads and by using a plurality of magnetic beads coated with major facilitator superfamily domain-containing protein antibody;
   (c) staining the concentrated circulating brain microvascular endothelial cells with a conjugated antibody, the conjugated antibody being a Fluorescein isothiocyanate (FITC) conjugated CD146 antibody;
   (d) counting the number of the stained brain microvascular endothelial cells; and (e) determining that the human subject has traumatic brain injury when a density of the circulating brain microvascular endothelial cells is greater than 90 count per milliliter.

2. A method for diagnosing a brain microbial infection, the method comprising:
(a) obtaining a peripheral blood sample from a human subject;
(b) concentrating circulating brain microvascular endothelial cells from the peripheral blood sample sequentially by using a plurality of lectin coated magnetic beads and by using a plurality of magnetic beads coated with major facilitator superfamily domain-containing protein antibody;
(c) staining the concentrated circulating brain microvascular endothelial cells with a conjugated antibody, the conjugated antibody being a Fluorescein isothiocyanate (FITC) conjugated CD146 antibody;
(d) counting the number of the stained brain microvascular endothelial cells; and
(e) determining that the human subject has brain microbial infection when a density of the circulating brain microvascular endothelial cells is greater than 90 count per milliliter.

3. A method for diagnosing blood brain barrier injury, the method comprising:
(a) obtaining a peripheral blood sample from a human subject;
(b) concentrating circulating brain microvascular endothelial cells from the peripheral blood sample sequentially by using a plurality of lectin coated magnetic beads and by using a plurality of magnetic beads coated with major facilitator superfamily domain-containing protein antibody;
(c) staining the concentrated circulating brain microvascular endothelial cells with a conjugated antibody, the conjugated antibody being a Fluorescein isothiocyanate (FITC) conjugated CD146 antibody;
(d) counting the number of the stained brain microvascular endothelial cells; and
(e) determining that the human subject suffers an injury to his blood brain barrier when a density of the circulating brain microvascular endothelial cells is greater than 90 count per milliliter.

* * * * *

UNITED STATES PATENT AND TRADEMARK OFFICE
CERTIFICATE OF CORRECTION

PATENT NO.        : 11,054,422 B2
APPLICATION NO.   : 16/431559
DATED             : July 6, 2021
INVENTOR(S)       : Sheng-He Huang Page 1 of 1

It is certified that error appears in the above-identified patent and that said Letters Patent is hereby corrected as shown below:

In the Specification

Column 12, Lines 63-64, the circled "R" after the word Dynabeads should read --TM--.

Column 13, Line 56, the word "Dynabeads" should read --magnetic beads--; Column 13, Line 57, the word "The beads" should read --Dynabeads TM beads--; Column 13, Line 61, the word "beads/mi" should read --beads/ml--; Column 13, Line 63, the word "Dynabeads" should read --Dynabeads TM--.

Column 14, Lines 5 to 6, the word "Msd2a-precoated Dynabeads" should read --Msd2a antibody-precoated Dynabeads TM--; Column 14, Line 6, the word "Dynabeads" should read --Dynabeads TM--.

Column 15, Line 31, the circled "R" after the word Blocker should read "TM".

Signed and Sealed this
Twenty-ninth Day of March, 2022

Drew Hirshfeld
*Performing the Functions and Duties of the*
*Under Secretary of Commerce for Intellectual Property and*
*Director of the United States Patent and Trademark Office*